United States Patent [19]

Jerath

[11] Patent Number: 5,047,042
[45] Date of Patent: Sep. 10, 1991

[54] CERVICAL CONIZATION METHOD AND INSTRUMENT

[76] Inventor: Ravinder Jerath, 2100 Central Ave., Augusta, Ga. 30909

[21] Appl. No.: 477,548

[22] Filed: Feb. 9, 1990

[51] Int. Cl.$^5$ .............................................. A61B 17/32
[52] U.S. Cl. ..................................... 606/167; 128/751
[58] Field of Search .............. 606/180, 167, 170, 174, 606/205, 206, 207; 604/22; 128/749, 750, 751; 30/136, 300, 310

[56] References Cited

U.S. PATENT DOCUMENTS

| | | |
|---|---|---|
| 2,541,246 | 7/1948 | Held . |
| 2,568,234 | 3/1949 | Haufrect . |
| 2,668,537 | 2/1954 | Kapp . |
| 2,827,039 | 7/1956 | Seiger . |
| 3,147,749 | 9/1964 | Marsh .................................. 128/751 |
| 3,345,981 | 10/1967 | Hodges .............................. 606/170 |
| 3,357,422 | 12/1967 | Creelman ........................... 128/751 |
| 3,628,522 | 12/1971 | Kato .................................... 30/300 |
| 3,943,916 | 3/1976 | Vadas .................................. 128/751 |
| 4,369,788 | 1/1983 | Goald .................................. 128/321 |
| 4,559,944 | 12/1985 | Jaeger ................................. 606/205 |
| 4,600,007 | 7/1986 | Lahodny et al. .................... 128/318 |
| 4,655,223 | 4/1987 | Kim .................................... 128/334 R |

FOREIGN PATENT DOCUMENTS

| | | | |
|---|---|---|---|
| 062461 | 9/1978 | U.S.S.R. .............................. | 606/170 |
| 0791375 | 12/1980 | U.S.S.R. .............................. | 128/751 |

Primary Examiner—C. Fred Rosenbaum
Assistant Examiner—William W. Lewis
Attorney, Agent, or Firm—Thomas, Kerr & Kayden

[57] ABSTRACT

A surgical instrument for performing a uterine cervical conization has a pair of elongated arms pivotally connected together intermediate their ends for scissor-like relative motion. One arm includes a coextensive probe at one end sized to be inserted through the cervical canal. The corresponding end of the other arm secures a cutter in position forming an acute cutting angle relative to the probe with the apex of the angle located adjacent to the distal end of the probe. Locking means is provided for releasably locking the arms in at least one predetermined relative pivotal position and consequently the cutter at a corresponding predetermined cutting angle relative to the probe. In use, the probe is inserted through the cervical canal with the cutter piercing the cervical tissue. At a sufficient depth, the arms and cutter are locked into position and the instrument is rotated about the axis of the probe to excise a cone-shaped tissue sample from about the mouth of the uterine cervix.

9 Claims, 2 Drawing Sheets

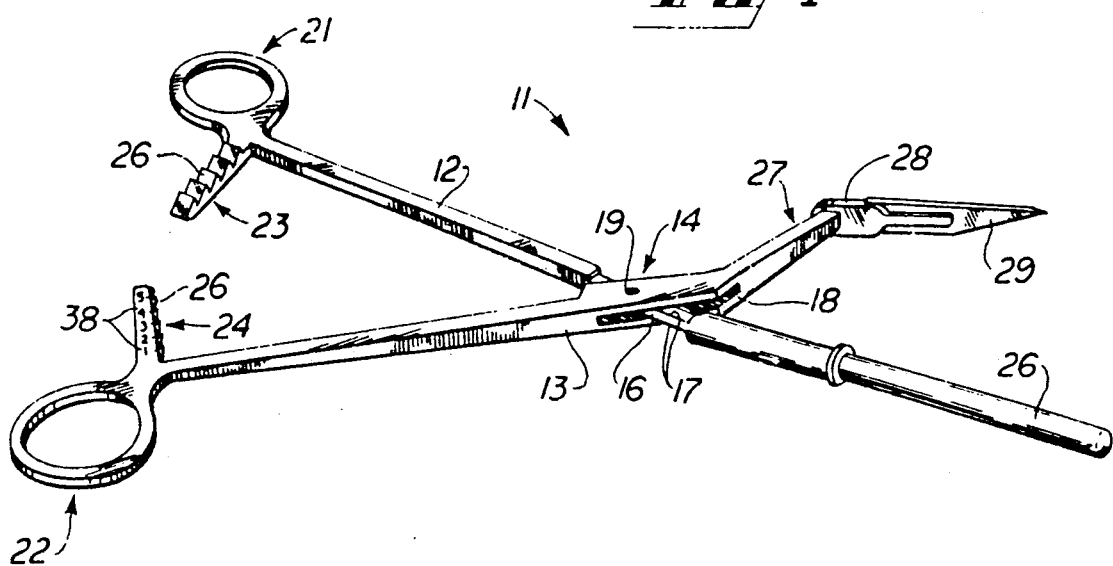
Fig 1
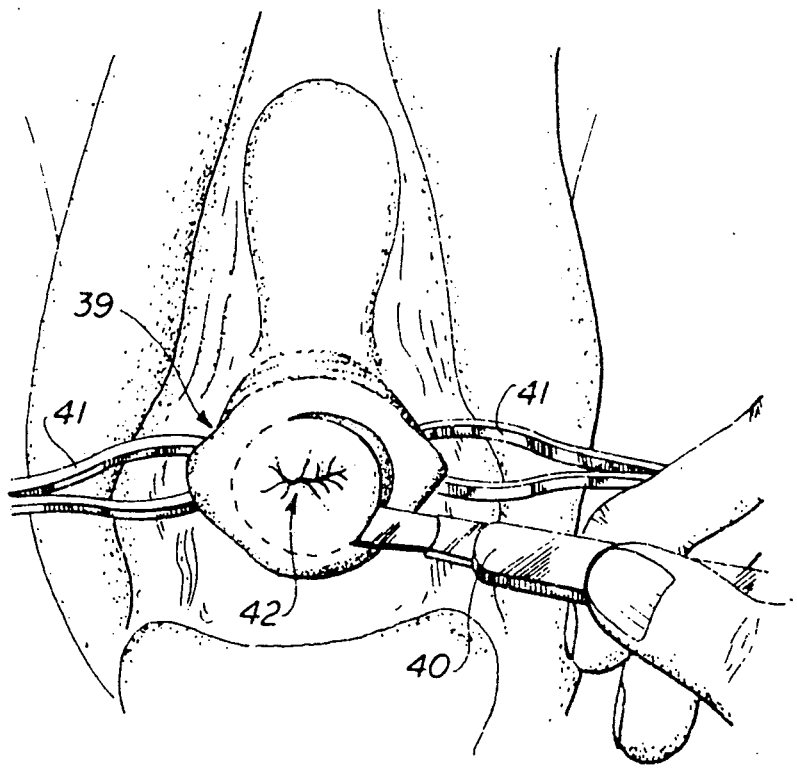
Fig 2
(PRIOR ART)
Fig 6

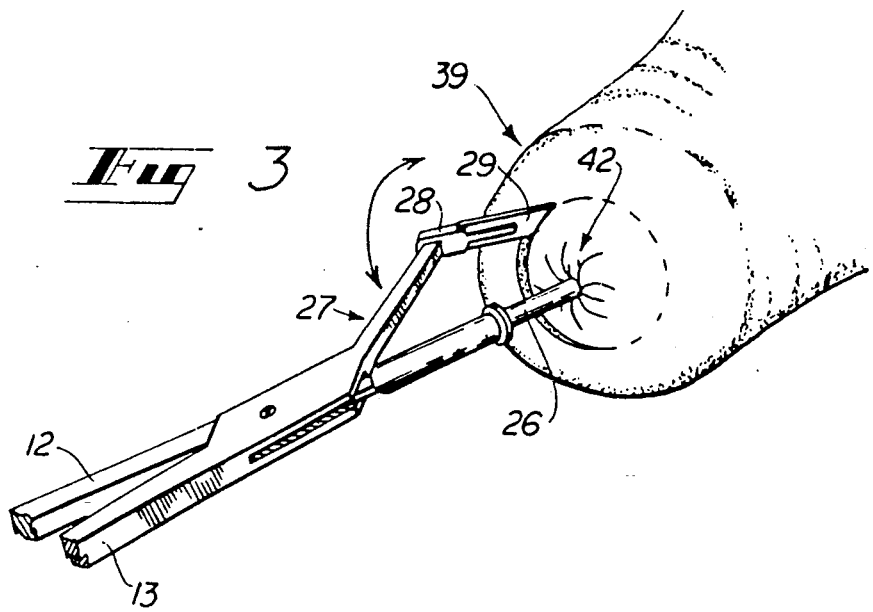
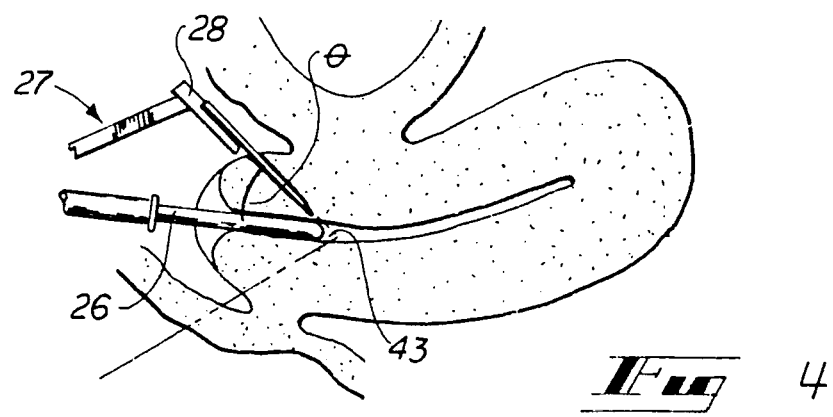
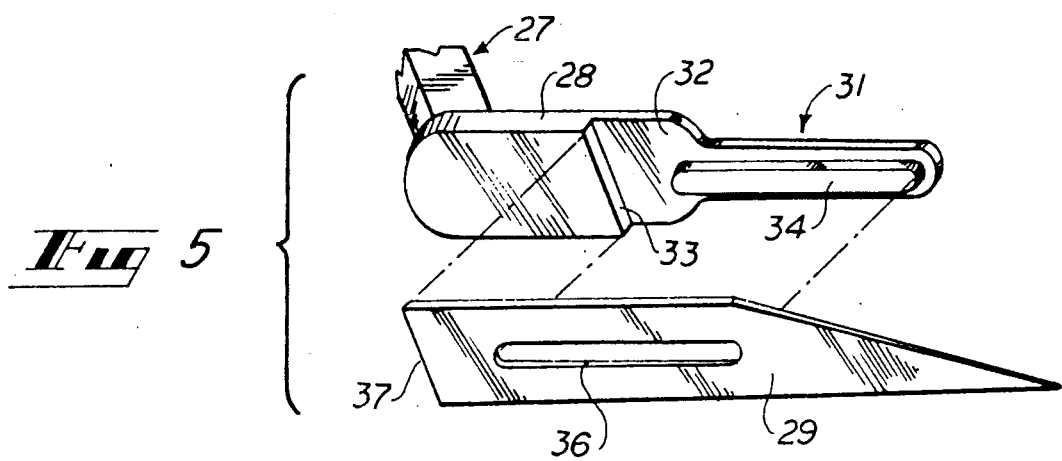

CERVICAL CONIZATION METHOD AND INSTRUMENT

TECHNICAL FIELD

This invention relates generally to surgical methods and instruments and particularly to a method and instrument for performing a uterine cervical conization.

BACKGROUND OF THE INVENTION

Uterine cancer has long been a dreaded and sometimes fatal form of cancer that can attack women particularly during mid-life. In order to detect such cancer in its early stages and thus enhance the chances of successful treatment, most women periodically undergo a uterine pap smear test. In such tests, a small amount of tissue typically is scraped from the interior walls of the uterus and the uterine cervix and pathologically examined to determine if abnormal or pre-cancerous cells are present. The results of a pap smear test are usually designated as falling into one of three classes with class 1 corresponding to a normal pap smear, class 2 corresponding to the presence of inflamed cells in the uterine tissue and class 3 indicating the discovery of diaplastic or premalignant cells. The great majority of pap smear results fall into classes 1 and 2.

For class 3 pap smears where the presence of some cancer within the uterine tissue is indicated, most gynecologists recommend more extensive tests to determine whether cancer is indeed present and if so its extent and severity. Such tests usually include a surgical procedure known as a uterine cervical conization in which a cone-shaped plug or tissue sample is cut by a surgeon from about the mouth of the cervix and delivered to a pathologist for analysis. The accuracy and reliability of the pathological analysis of the sample and consequently of the gynecologist's ultimate prognosis is highly dependent upon the regularity and symmetry of the particular sample being examined. The ideal sample, for example, is a cleanly cut cone that has a constant cone angle about its circumference and that is symmetric about the central canal of the cervix from which it has been excised.

In the past, the cervical conization procedure has been performed by surgeons using a free hand method wherein a standard surgical scalpel is inserted through the vagina to the uterine cervix and carefully manipulated to excise the sample from about the mouth of the cervix. As can easily be understood, this method of excising the sample has long been plagued with problems and shortcomings and almost always results in an irregular and asymmetric tissue sample that, in turn, leads to less accurate and reliable analytical results. The location of the uterine cervix at the back of the vagina, for example, makes convenient access difficult and the surgeon is usually forced to grasp the scalpel far from the cutting blade such that precise scalpel control becomes difficult. This problem is further exacerbated by the necessity that the surgeon be able to observe the procedure carefully as it is performed to assure the most accurately shaped sample possible. Finally, the quality and particularly the symmetry of the sample has been highly dependent upon the skill and experience of the surgeon largely because the surgeon must simply "eyeball" or estimate the distance of the cut from the mouth of the cervix and the angle of the scalpel blade with respect to the cervical canal as the procedure progresses. Even the most skilled surgeons have thus found it virtually impossible to extract ideal tissue samples.

A continuing and heretofore unaddressed need exists, therefore, for a new surgical method and enabling instrument for performing a uterine cervical conization that will consistently produce cleanly cut, accurately shaped and highly symmetrical tissue samples for pathological analysis and that can easily be performed with a minimum of prior surgical training and experience. It is to the provision of such a method and apparatus that the present invention is primarily directed.

SUMMARY OF THE INVENTION

The present invention is a method and surgical instrument for performing a uterine cervical conization that consistently produces high quality tissue samples for analysis with a minimum of required surgical skill and experience. The instrument is embodied in a device that has a pair of arms hingedly connected intermediate their ends in scissor-like fashion with the arms being provided at one of their mutually corresponding ends with finger receiving loops for grasping and manipulation. The opposite end of one of the arms includes an elongated rod-shaped probe sized to be inserted into the central canal of the uterine cervix. The opposite end of the other arm is formed to receive and hold a surgical blade in spaced angled relationship relative to the probe with the cutting edge of the blade forming an acute cutting angle relative to the probe, the apex of the cutting angle being located adjacent the distal end of the probe. A pair of confronting adjustably and releasably interlocking tabs are provided on the arms adjacent the finger receiving loops for releasably locking the surgical blade in a selected one of a number of predetermined orientations relative to the probe.

In performing the method of the invention, the instrument is grasped in scissor like fashion and moved through a patient's vagina with the probe being inserted through the mouth of the uterine cervix at the back of the vagina. As the probe moves through the cervical canal, the blade tip is positioned by appropriate pivotal manipulation of the arms to pierce the cervix at a desired distance from its mouth. As the probe and blade move further, the instrument is slowly closed and locked with the locking tabs so that the blade forms a desired cutting angle relative to the probe. With the instrument thus in place, it is gently rotated about the axis of the probe such that the blade follows a circular path about the probe and, since the blade is angled relative to the probe, cuts a conical-shaped plug or tissue sample from about the cervical mouth for pathological analysis. Since the blade is locked to define a fixed cutting angle relative to the probe, the resulting sample forms a precise cone that is symmetric about the cervical canal and that has cleanly cut outside walls. Minimum skill and prior experience is required of the surgeon since the accuracy of the procedure is assured by the surgical instrument itself and is not dependent upon personal ability of the surgeon.

Thus, it is an object of the invention to provide a method and surgical instrument for performing a uterine cervical conization that consistently produces clean cut, accurately shaped and symmetrical tissue samples for pathological analysis.

It is a further object of the invention to provide a surgical procedure for performing a cervical conization that can easily by mastered by a surgeon without need for extensive training or experience.

A still further object of the invention is to provide a surgical instrument for performing a cervical conization that is simply constructed for reliability and economy.

These and other objects, features and advantages of the invention will become more apparent upon review of the following detailed description taken in conjunction with the accompanying drawings.

BRIEF DESCRIPTION OF THE DRAWINGS

FIG. 1 is a perspective view of a surgical instrument that embodies principals of the invention in a preferred form.

FIG. 2 illustrates the prior art surgical procedure for performing a uterine cervical conization.

FIG. 3 illustrates a cervical conization as performed by the method and instrument of the present invention.

FIG. 4 is a cross sectional view of a uterus and uterine cervix illustrating extraction of a cone-shaped tissue sample by the method and instrument of the invention.

FIG. 5 is a perspective view illustrating one method of mounting a surgical blade to the surgical instrument of the invention.

FIG. 6 is a partial plan view of the adjustably locking tabs of the instrument of the present invention.

DETAILED DESCRIPTION OF THE PREFERRED EMBODIMENT

Referring now to the drawings in which like numerals represent like parts throughout the several views, FIG. 1 illustrates a surgical instrument 11 that embodies principals of the invention in a preferred form. The instrument is seen to comprise first and second elongated arms 12 and 13 that are pivotally connected together intermediate their ends at 14 for scissor-like relative motion of the arms. Specifically, in the illustrated embodiment the first arm 12 is formed with a reduced diameter portion 16 that has opposed flattened surfaces 17 that extend through a slot 18 formed in the second arm 13. A pin or screw 19 extends through both arms at 14 such that the arms can be mutually pivoted relative to each other about the pin 19 in scissor-like fashion.

Finger receiving loops 21 and 22 are formed at a corresponding end of each arm 12 and 13 respectively and are sized to receive the fingers of a user of the instrument for grasping and manipulation thereof. A pair of tabs 23 and 24 extend inwardly from the arms 12 and 13 in mutually confronting relationship and each tab is formed with ratchet teeth 26 that are configured and oriented for mutual releasable locking engagement as the arms are pivoted toward each other. With this largely conventional arrangement, the arms can be releasably locked in a number of predetermined pivotal positions relative to each other for purposes explained hereinbelow.

An elongated cylindrical probe 26 is mounted at one end to the other end of the first elongated arm 12 and extends therefrom in a direction substantially coextensive with the arm. In practice, the probe 26 can be independently manufactured and secured to the arm 12 as by welding or alternatively formed as an integral part of the arm itself if desired. The probe 26 is sized to be received snuggly within the canal of a female uterine cervix for performing a cervical conization as detailed more fully hereinbelow.

The corresponding end of the second arm 13 is formed with an offset portion 27 that extends generally from the pivotal connection 14 of the arms. Mounted to the distal end of the offset portion 27 is a cutting blade mounting shoe 28 that is configured for receiving and securing a surgical cutting blade 29 as shown. In this regard, and as illustrated in FIG. 5, the shoe 28 includes an extending tang 31 formed with an inset blade engaging surface 32 that defines a canted ridge 33 with the body of the mounting shoe 28. A raised tongue 34 extends along the length of the tang 31 and is sized and positioned to be received snuggly within an elongated slot 36 formed in a standard surgical scalpel blade when the rear edge 37 of the blade is in firm abutting relationship with the ridge 33. With this arrangement, a common disposable surgical blade can be releasably secured to the mounting shoe 28 by abutting the rear edge of the blade against the ridge 33 and "snapping" the blade into position with the tongue 34 extending through and being firmly seated within the blade slot 36.

With an instrument of the just described configuration it will be appreciated that the blade 29 can alternately be moved toward and away from the probe 26 by appropriate pivotal manipulations of the arms 12 and 13. As best illustrated in FIGS. 3 and 4, when the arms are pivoted to bring the blade and probe toward engagement, the cutting edge of the blade forms an acute cutting angle relative to the probe with the apex of the angle located adjacent to the distal end of the probe. Further, both the distance between the blade and probe and the magnitude of the cutting angle can be varied by pivotal adjustment of the arms 12 and 13 with a number of predetermined ones of these relationships being releasably lockable by virtue of the opposing locking tabs 23 and 24. Indicia 38 can be provided on the tabs if desired as an indication to the user of particular distance and angular relationships between the blade 29 and probe 26 that can be selected and locked into position by operation of the tabs 23 and 24.

FIG. 2 illustrates a common prior art method of performing a uterine cervical conization to excise a cone-shaped tissue sample from about the mouth of the cervix. In performing such prior art procedures, the vagina is typically parted to reveal the uterine cervix 39 and the cervix is secured in place with appropriate surgical clamps 41, 41. A standard scalpel 40 is then inserted through the vagina to the mouth of the cervix where the blade is moved by the surgeon in a circular pattern about the mouth 42 of the cervix 39 while attempting to maintain the blade at a constant acute angle relative to the cervical canal 43 (FIG. 4). As detailed hereinabove, such procedures, because of their inherent inaccuracies, tend to produce irregularly shaped and asymmetric tissue samples that degrade the reliability of subsequent pathological analysis.

FIGS. 3 and 4 illustrate use of the instrument of the present invention to perform a uterine cervical conization procedure. The probe 26 is first inserted through the mouth 42 of the cervix 39 and into the cervical canal 43. As the probe moves deeper into the cervix, the arms 12 and 13 are mutually pivoted to cause the blade 29 to pierce the cervical tissue at a desired location spaced from the mouth 42 of the cervix 39. Upon further movement of the probe 26 into the cervical canal, the arms are slowly pivoted toward each other to bring the blade 29 closer to the probe 26 as it slices through the cervical tissue. As the blade 29 approaches the probe 26, the ratchet teeth of the confronting tabs 23 an 24 come into engagement and the surgeon can thereby releasably lock the blade in position defining a desired cutting angle relative to the probe to produce a tissue sample of corresponding desired cone angle. The particular desired setting will generally depend among other factors upon the size of the cervix and extent of expected cancer therein.

With the probe in position within the cervical canal and the blade locked to define a desired cutting angle, the instrument can be rotated gently about the longitudinal axis of the probe 26 to move the blade in a circular pattern about the probe and cervical canal. In some instances, the surgeon may wish to insert the blade and probe part way into the cervix and rotate the instrument for an initial shallow cut after which the blade and probe can be fully inserted and appropriately adjusted for the final cut. Since the cervical tissue typically is very firm, the canal walls tend to maintain the probe securely in place within the canal. In this way, the blade is confined to its circular path of movement about the cervical canal to cut a clean precisely formed cone of tissue that is highly symmetric about the cervical canal. When the blade has traversed a complete circle, the resulting excised cone-shaped tissue sample can be removed from the cervix for delivery to the pathologist and the cervix sutured in the normal way for healing.

It can easily be realized from the forgoing discussion that the method and apparatus of the present invention represents a vast improvement over manual procedures heretofore employed. The quality of the tissue sample produced is highly superior to that produced by prior art methods because of its clean cut accurately angled surfaces and its symmetry about the axis of the cervical canal. Further, such high quality tissue samples are produced reliably and consistently and since the spacing and cutting angle formed by the blade are securely fixed, much less surgical skill and training is required to perform a cervical conization than with prior art methods.

The invention has been described in terms of preferred embodiments that function in preferred ways to perform the object procedure. It will be obvious to skilled artisans, however, that many departures from the preferred embodiments might be made with comparable results. A cutting laser or reciprocating blade for example might be substituted for the blade of the preferred embodiment such that the term "cutter" as used herein should be considered to encompass any means for severing the cervical tissue. Further, although the probe and blade have been illustrated attached to ends of scissor arms, it will be obvious that they might be mounted to many various types of support frames that could maintain the desired spatial relationship between the cutter and probe. The probe could also be formed longer or shorter than illustrated such that the apex of the cutting angle would fall along the axis of the probe at a position displaced from its distal end. These and other additions, deletions and modifications might be made to the preferred embodiments without departing from the spirit and scope of the invention as set forth in the claims.

What is claimed is:

1. A surgical instrument for excising a cone shaped tissue sample with said surgical instrument comprising:
    a frame;
    an elongated probe mounted at one end to said frame and extending therefrom;
    a cutter; and
    securing means on said frame for securing said cutter thereto with the cutter forming an acute cutting angle relative to said elongated probe, said cutting angle having its apex adjacent to the distal end of said probe;
    said frame including first and second elongated arms pivotally attached together intermediate their ends for scissor-like relative motion of said arms, said elongated probe being mounted to one end of said first arm and said securing means being mounted to the corresponding end of said second arm.

2. A surgical instrument as claimed in claim 1 wherein said corresponding end of said second arm is formed with an offset that bears said securing means.

3. A surgical instrument as claimed in claim 1 and further comprising locking means in said instrument for releasably locking said arms in at least one pre-determined pivotal orientation with respect to each other.

4. A surgical instrument as claimed in claim 3 wherein said locking means comprises a pair of confronting tabs mounted to said arms with said tabs bearing sets of ratchet teeth configured and arranged for cooperative locking engagement as said arms are pivoted toward mutual engagement.

5. A surgical instrument as claimed in claim 1 and further comprising finger receiving means on the other ends of said first and second arms for grasping and manual pivotal manipulation of said arms.

6. A surgical instrument, as claimed in claim 5 wherein each of said finger receiving means comprises a ring formed on the end of its corresponding arm with each ring being sized to receive at least one finger of a user of said instrument.

7. A surgical instrument for performing a uterine cervical conization with said surgical instrument comprising:
    first and second elongated arms pivotally attached together intermediate their ends for relative pivotal motion of said arms;
    an elongated substantially cylindrical probe mounted at one end to an end of said first elongated arm and extending therefrom with said probe being substantially coextensive with said first elongated arm and sized to be inserted through a uterine cervical canal;
    a cutting blade, securing means mounted to the corresponding end of said second elongated arm with said securing means being configured for releasably securing said cutting blade in position with the cutting edge of the blade forming an acute cutting angle relative to said elongated probe, the acute cutting angle having its apex adjacent to the distal end of said probe;
    finger receiving rings formed on the opposite ends of said first and second arms for manual pivotal manipulation of said arms; and
    a pair of confronting tabs on said arms with each tab bearing a set of ratchet teeth configured for releasable locking engagement with the teeth of the other tab as said arms are pivoted toward mutual engagement,
    whereby the probe can be inserted through the uterine cervical canal and the arms pivoted toward each other and locked to form a desired cutting angle between the blade edge and the probe whereupon the instrument can be rotated about the axis of the probe to excise a cone shaped tissue sample from about the mouth of the cervix.

8. A method of performing a uterine cervical conization by means of an instrument having first and second arms each having distal and proximal ends with the arms being pivotally connected together between their ends, the first arm having a probe member affixed to the distal end thereof and the second arm having a cutter member affixed to the distal end thereof and oriented at an angle relative to the probe member, the method comprising the steps of:

(a) inserting the cutter into the body of the cervix;

(b) inserting the probe member into the cervical canal and securing the cutter in position within the body of the cervix adjacent the mouth of the cervix with the cutter forming an acute cutting angle relative to the cervical canal by moving the proximal ends of the arms towards each other until a desired cutting angle and position are achieved;

(c) rotating the cutter and probe about the axis of the cervical canal while monitoring the desired acute cutting angle formed by the cutter and probe to sever a cone-shaped tissue sample from the cervix; and (d) removing the cone-shaped tissue sample from the cervix.

9. The method of claim 8 wherein the cutter is fixed relative to the probe by the step of locking the proximal ends of the arms to each other.

* * * * *